United States Patent [19]
Grub et al.

[11] Patent Number: 5,266,592
[45] Date of Patent: Nov. 30, 1993

[54] COMPOSITIONS WHICH HAVE A PHYSIOLOGICAL COOLING EFFECT, AND ACTIVE COMPOUNDS SUITABLE FOR THESE COMPOSITIONS

[75] Inventors: Helmut Grub, Holzminden; Ralf Pelzer, Fürstenberg; Rudolf Hopp, Holzminden; Roland Emberger, Holzminden; Heinz-Jürgen Bertram, Holzminden, all of Fed. Rep. of Germany

[73] Assignee: Haarmann & Reimer GmbH, Holzminden, Fed. Rep. of Germany

[21] Appl. No.: 862,851

[22] Filed: Apr. 3, 1992

[30] Foreign Application Priority Data

Apr. 5, 1991 [DE] Fed. Rep. of Germany ....... 4110973

[51] Int. Cl.$^5$ ............................................. A61K 31/335
[52] U.S. Cl. .................................. 514/452; 514/450; 514/462; 514/467; 514/901; 424/48; 424/49
[58] Field of Search ............... 514/452, 462, 467, 450; 424/49, 48; 549/333, 341, 374

[56] References Cited

U.S. PATENT DOCUMENTS

| | | |
|---|---|---|
| 3,096,345 | 7/1963 | Heckenbleikner et al. . |
| 3,206,474 | 9/1965 | Heckenbleikner et al. . |
| 3,257,480 | 6/1966 | Hechenbleikner et al. . |
| 3,349,150 | 10/1967 | Hechenbleikner et al. . |
| 3,830,930 | 8/1974 | Moeller et al. . |
| 3,917,613 | 11/1975 | Humbert et al. . |
| 3,991,178 | 11/1976 | Humbert et al. . |
| 4,032,661 | 6/1977 | Rowsell et al. . |
| 4,033,994 | 7/1977 | Watson et al. . |
| 4,059,118 | 11/1977 | Watson et al. . |
| 4,070,449 | 1/1978 | Rowsell et al. . |
| 4,070,496 | 1/1978 | Rowsell et al. . |
| 4,136,163 | 1/1979 | Watson et al. . |
| 4,150,052 | 4/1979 | Watson et al. . |
| 4,153,679 | 5/1979 | Rowsell et al. . |
| 4,157,384 | 1/1979 | Watson et al. . |
| 4,178,459 | 12/1979 | Watson et al. . |
| 4,190,643 | 2/1980 | Watson et al. . |
| 4,193,936 | 3/1980 | Watson et al. . |
| 4,226,988 | 10/1980 | Watson et al. . |
| 4,230,688 | 10/1980 | Rowsell et al. . |
| 4,296,093 | 10/1981 | Rowsell et al. . |
| 4,296,255 | 10/1981 | Watson et al. . |

FOREIGN PATENT DOCUMENTS

| | | |
|---|---|---|
| 0080148 | 6/1983 | European Pat. Off. . |
| 0485170 | 5/1992 | European Pat. Off. . |
| 2022369 | 11/1971 | Fed. Rep. of Germany . |
| 2608226 | 9/1977 | Fed. Rep. of Germany . |
| 1422998 | 1/1976 | United Kingdom . |

OTHER PUBLICATIONS

V. Boekelheide et al, "Drugs Effecting Muscular Paralysis." J. of Am. Chem. Soc., vol. 71, No. 10, (1949), pp. 3303–3307.

*Primary Examiner*—Nicky Chan
*Attorney, Agent, or Firm*—Sprung Horn Kramer & Woods

[57] ABSTRACT

Ketals, preferably glycerol ketals such as, for example, 1-menthone glycerol ketal or 3,3,5-trimethylcyclohexanone glycerol ketal, have a physiological cooling effect and are therefore suitable as active compounds in compositions which are intended to cause a sensation of freshness on human skin or mucous membrane.

5 Claims, No Drawings

COMPOSITIONS WHICH HAVE A PHYSIOLOGICAL COOLING EFFECT, AND ACTIVE COMPOUNDS SUITABLE FOR THESE COMPOSITIONS

The invention relates to compositions which do not have an interfering odour and taste and which cause a physiological cooling effect when applied to the skin or the mucous membranes. It seems that the effect which conveys to the person concerned a sensation of freshness can be attributed to stimulation of the corresponding receptors of the human nervous system. The invention furthermore relates to new compounds which are capable of causing this effect.

The best known natural compound which has a physiological cooling effect is, without doubt, (−)-menthol, which is a component of peppermint oil (ex Mentha arvensis). It is employed, for example, for manufacturing dentifrices, mouth washes, foodstuffs, beverages and cosmetics. However, the typical strong peppermint flavour and the bitter and stinging taste are frequently found unpleasant.

There has therefore been no lack of attempts to find substances which have the positive cooling effect without the abovementioned shortcomings of menthol. For example, German Offenlegungsschrift 2,202,535 proposes p-menthane-3-carboxamide and esters of p-menthane-3-carboxylic acid, German Offenlegungsschrift 2,205,255 proposes N-substituted p-menthane-3-carboxamides, German Offenlegungsschrift 2,317,538 proposes aliphatic amides, German Offenlegungsschrift 2,334,985 proposes cyclic and acyclic sulphoxides and sulphones, and German Offenlegungsschrift 2,345,156 proposes aliphatic substituted phosphine oxides. However, these compounds do not occur naturally and are also not degraded by the human organism to give substances which occur in nature. Consequently the use of these substances in foodstuffs can be considered as being questionable.

Menthol derivatives have also been investigated; however, they do not completely meet the set requirements. For example, 1-menthylethyl carbonate, which has been proposed in German Offenlegungsschrift 2,022,364, smells of oranges, menthyl N-acetylglycinate, which has been proposed in German Offenlegungsschrift 2,433,165, and the menthol esters of heterocyclic carboxylic acids, which have been proposed in German Offenlegungsschrift 2,339,661, are bitter, and some of the menthyl keto esters which have been proposed in U.S. Pat. No. 3,830,930 are bitter over a prolonged period and their cooling effect is only poor.

German Offenlegungsschrift 2,608,226 discloses menthol esters of naturally occurring $C_2-C_6$-hydroxycarboxylic acids (which, in turn, may be esterified on the hydroxyl group with $C_1-C_4$-carboxylic acids), which are odourless and flavourless and have a prolonged cooling effect. 1-Menthyl lactate, in particular, has proven itself in practice. However, the product is not stable to alkalis, so that it is not suitable for all types of application (for example soaps).

Other products too are already being employed in practice, for example 3-1-menthoxypropane-1,2-diol (European Patent Specification 80,148) and N-ethyl-p-menthane-3-carboxamide (German Offenlegungsschrift 2,205,255 and 2,413,639). However, there was a demand for compositions with an increased cooling effect or a better price/performance ratio.

Surprisingly, it has now been found that selected ketals have the desired advantageous combination of desirable properties.

The invention relates to compositions which have a physiological cooling effect and which contain at least one ketal of the formula

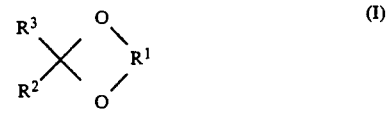

in which
$R^1$ represents a $C_2-C_6$-alkylene radical having at least 1, but not more than 3, hydroxyl group(s), preferably 1 hydroxyl group, and
either $R^2$ and $R^3$ independently of one another represent $C_1-C_{10}$-alkyl which is optionally substituted by 1 to 3 radicals selected from the group comprising hydroxyl, amino and halogen (such as fluorine, chlorine, bromine or iodine), $C_5-C_7$-cycloalkyl, preferably cyclohexyl, $C_6-C_{12}$-aryl, preferably phenyl, with the proviso that the total of the C atoms of $R^2$ and $R^3$ is not less than 3,
or $R^2$ and $R^3$ together represent an alkylene radical which, together with the carbon atom which carries the radicals $R^2$ and $R^3$, forms a 5–7-membered ring, it being possible for this alkylene radical, in turn, to be substituted by $C_1-C_6$-alkyl groups.

Preferred radicals $R^2$ and $R^3$ comprise methyl, isopropyl and tert.-butyl.

The length of the radicals $R^2$ and $R^3$ influences the effect of the compounds I: shorter radicals lead to an immediate, short effect; longer radicals lead to a delayed, but prolonged effect. An important aspect for the cosmetics industry is the solubility of the compounds in water; this is the case, in particular, with short radicals $R^2$ and $R^3$.

Preferred radicals $R^1$ embrace 1,2- and 1,3-alkylene radicals which, together with the two oxygen atoms and with the carbon atom to which the two oxygen atoms are attached, form a dioxolane or dioxane ring.

Preferred compounds I in which $R^2$ and $R^3$ together represent an alkylene radical are those of the formula

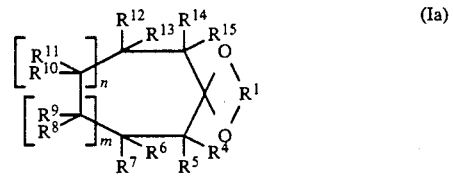

in which
$R^4$ to $R^{15}$ independently of one another denote hydrogen or $C_1-C_6$-alkyl, preferably hydrogen or $C_1-C_4$-alkyl, and
m and n independently of one another denote zero or 1.

Preferred compounds of the formula Ia are those in which the total of m+n is 1, i.e. ketals of an optionally substituted cyclohexanone.

Preferred substituents, of which there may be present, in particular, 1 to 3, are methyl, isopropyl and tert.-butyl.

The ketals I are either known, or they have not been known to date and can be prepared by analogous, known processes. For example, ketal I will generally be prepared by acid-catalysed reaction of the ketone on which ketal I is based and not less than the equivalent amount of aliphatic $C_3$-$C_6$-alcohol having not less than 3 and not more than 5, preferably 3, hydroxyl groups. In general, the ketone on which ketal I is based and not less than 0.5 mol equivalents, but, as a rule, a 1.2- to 4-fold, preferably 1.5- to 3-fold excess of this amount of the $C_3$-$C_6$-alcohol having 3 to 5 hydroxyl groups will be employed. Examples of acid catalysts which can be used are p-toluenesulphonic acid, phosphoric acid or potassium hydrogen sulphate in catalytically effective amounts (for example 0.1 to 3 g of p-toluenesulphonic acid per mole of ketone). The reaction will preferably be carried out either in an organic solvent which together with water forms an azeotrope, so that the water, which is liberated during the formation of the ketal, can be eliminated by azeotropic entrainment, or water-consuming coreagents such as, for example, trialkyl ortho esters are used. Examples of preferred organic solvents comprise benzene, toluene, xylene, chloroform, methylene chloride and trichloroethylene. The reaction can be regarded as complete when water no longer separates out or when an ester/alcohol mixture is no longer separated out. It is recommended to wash the products subsequently with dilute alkali and with water, to separate and dry the organic phase, to strip off the solvent and, if appropriate, to purify the residue, for example by distillation.

Particularly preferred ketals I are those of the formulae

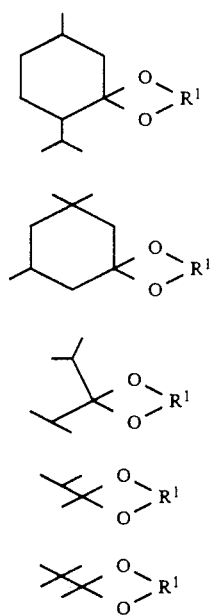

in which $R^1$ has the abovementioned meaning and preferably stands for

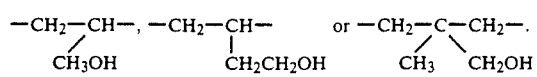

Ketals from glycerol and its homologues are particularly preferred.

The invention also relates to the ketals III to VI.

The ketals I to be employed in the compositions according to the invention can have asymmetric C atoms; optical isomerism can therefore occur. Depending on the starting material and the preparation methods used, they can exist in the form of mixtures of the optical isomers or in the form of pure isomers. The cooling effect of the isomers may differ, so that one or the other isomer may be preferred.

Besides the ketals I, the compositions according to the invention may contain carriers and/or diluents. The nature of these depends on the intended use of the composition.

The compositions according to the invention can be used for all purposes where a physiological cooling effect is desired. Examples of products in which such coolants are frequently used are luxury items such as chewing gum, chewing tobacco, cigarettes, beverages, ice cream, confectionary, fats used in the manufacture of wafers, pharmaceutical preparations, body care products or cosmetic preparations such as dentrifices, mouth washes, preparations for gargling, perfumes, powders, lotions, ointments, oils, creams, shaving foam, aftershaves, shampoos etc.

The ready to use products contain the ketals I in an amount which is sufficient for provoking the desired sensation of cold. As a rule, 0.01 to 3, preferably 0.05 to 1, per cent by weight are used relative to the weight of the ready to use product (e.g. toothpaste, mouthwash).

The examples which follow illustrate the invention. Unless otherwise indicated, percentages are per cent by weight.

EXAMPLES

Example 1: 1-Menthone glycerol ketal (known from Svishchuk, A. A.; Makhnovskii, N. K.; Mikryukova, N.Kh. Ukr. Khim. Zh. (Russ. Ed.) 43(2), 173-6, 1977 CA 87(5); 39667u)

In a 2 l three-necked flask there are introduced 308 g of 1-menthone (2 mol), 276 g of glycerol (3 mol) and 5 g of potassium hydrogen sulphate in toluene. This mixture is refluxed in a water separator. After 7 hours, 42 g of water have separated. The mixture is neutralised and distilled.

At 104°-106° C./1 mbar, 441 g of a colourless, clear liquid distil over. Gas chromatography reveals that the purity is over 99%. According to the NMR spectrum, the resulting compound contains a 1,3-dioxolane ring.
$n_D^{20} = 1.4749; \alpha_D^{25} = -14.1°; d(25° C.) = 1.0380$.

Example 2: 3,3,5-Trimethylcyclohexanone glycerol ketal

A mixture of 140 g of 3,3,5-trimethylcyclohexanone (1 mol), 184 g of glycerol (2 mol) and 2 g of p-toluenesulphonic acid in toluene is treated as in Example 1.

At 70°-102° C./1.5 mbar, 235 g of a colourless, clear liquid distil over. Gas chromatography reveals that the purity is over 99%.

$n_D^{20} = 1.4699$; $d(25° C.) = 1.0369$; m.p. $< -20°$ C.

Examples 3-9:3-Methyl-2-butanone glycerol ketal

A mixture of 494 g of 3-methyl-2-butanone (5.75 mol), 529 g of glycerol (5.75 mol) and 4 g of p-toluenesulphonic acid is introduced into a reaction vessel and 670 g of trimethyl orthoformate (6.32 mol) are subsequently added dropwise. During this process, the temperature of the reaction mixture rises to approx. 45°-50°

C. The resulting methanol/methyl formate mixture is distilled off under atmospheric pressure to a bottom temperature of 100° C. It is then cooled to 50° C., a vacuum is applied slowly, and the mixture is subjected to fractional distillation under a high vacuum. Bulk: 716 g; $n_D^{20} = 1.4439$; d(25° C.)=1.0294.

Gas chromatography reveals that the purity is 97.5%.

The same process was also used for preparing the following compounds:

| Ex. | $R^2$ | $R^3$ | $n_D^{20}$ | d(25° C.) | Weight of the main fraction [g] |
|---|---|---|---|---|---|
| 4 | i-Butyl | Methyl | 1.4426 | 0.9995 | 748 |
| 5 | t-Butyl | Methyl | 1.4486 | 1.0160 | 821 |
| 6 | Ethyl | Ethyl | 1.4447 | 1.0330 | 667 |
| 7 | i-Propyl | i-Propyl | 1.4558 | 1.0167 | 830 |
| 8 | 1,5-Pentylene | | 1.4781 | 1.1117 | 807 |
| 9 | Methyl | Methyl | 1.4341 | 1.0655 | 667 |

Examples 3-8 relate to substances with cooling effect; Example 9 shows a substance without cooling effect.

Example 10: 1-Menthone 1.1.1-trimethylolethane ketal (=7-Isopropyl-3.10-dimethyl-1.5-dioxaspiro[5.5]undecan-3-methanol)

1-Menthone and 1.1.1-trimethylolethane were reacted in analogy to Example 1. A colourless high-viscous oil having the following properties was obtained: b.p.: 134° C.(1 mbar); $n_D^{20}$:1.4833; $\alpha_D^{25}$: −27.3°.

Example 11: 1-Menthone 1.1.1-trimethylolpropane ketal (=3-Ethyl-7-isopropyl-10-methyl-1.5-dioxaspiro [5.5]undecan-3-methanol)

1-Menthone and 1.1.1-trimethylolpropane were reacted in analogy to Example 1. A colourless high-viscous oil having the folloring properties was obtained: b.p.: 148° C.(1 mbar); $n_D^{20}$:1.4850; $\alpha_D^{25}$:−29.1°.

Example 12: 1-Menthone 1.2.4-butanetriol ketal (=6-Isopropyl-9-methyl-1.4-dioxaspiro[4.5]-decan-2-ethanol)

1-Menthone and 1.2.4-butanetriol were reacted in analogy to Example 1.

We claim:

1. A method of achieving a cooling effect on human skin or mucous membrane which comprises applying to such skin or mucous membrane an effective amount of a composition comprising at least one ketal of the formula

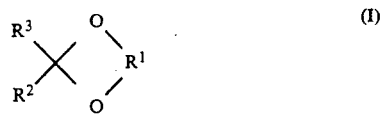

in which
$R^1$ represents a $C_2$-$C_6$-alkylene radical having at least 1, but not more than 3, hydroxyl group(s), and
either $R^2$ and $R^3$ independently of one another represent $C_1$-$C_{10}$-alkyl which is optionally substituted by 1 to 3 radicals selected from the group consisting of hydroxyl, amino and halogen, or $C_5$-$C_7$-cycloalkyl, or $C_6$-$C_{12}$-aryl, with the proviso that the total of the C atoms of $R^2$ and $R^3$ is not less than 3,
or $R^2$ and $R^3$ together represent an alkylene radical which, together with the carbon atom which carries the radicals $R^2$ and $R^3$, forms a 5-7 membered ring, said alkylene radical being unsubstituted or substituted by $C_1$-$C_6$-alkyl groups.

2. Method according to claim 1, where $R^1$ denotes a 1,2- or 1,3-alkylene radical.

3. Method according to claim 1, where $R^1$ denotes

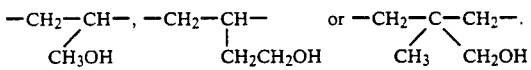

4. Method according to claim 1, where the ketal is one of the formula

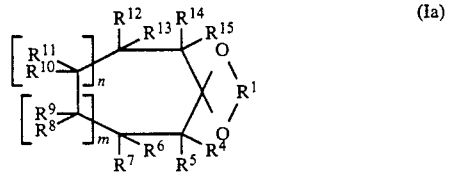

in which
$R^4$ to $R^{15}$ independently of one another denote hydrogen or $C_1$-$C_6$-alkyl and
m and n independently of one another denote zero or 1.

5. Method according to claim 4, where the total of m+n is 1.

* * * * *